(12) United States Patent
Sato et al.

(10) Patent No.: US 10,368,558 B2
(45) Date of Patent: Aug. 6, 2019

(54) LACTASE SOLUTION AND DAIRY PRODUCT USING SAME

(71) Applicant: Godo Shusei Co., Ltd., Tokyo (JP)

(72) Inventors: Tomoko Sato, Chiba (JP); Jun Yoshikawa, Chiba (JP); Hirofumi Horiguchi, Chiba (JP)

(73) Assignee: GODO SHUSEI CO., LTD., Tokyo (JP)

(*) Notice: Subject to any disclaimer, the term of this patent is extended or adjusted under 35 U.S.C. 154(b) by 0 days.

(21) Appl. No.: 15/532,633

(22) PCT Filed: Nov. 20, 2015

(86) PCT No.: PCT/JP2015/082784
§ 371 (c)(1),
(2) Date: Jun. 2, 2017

(87) PCT Pub. No.: WO2016/088589
PCT Pub. Date: Jun. 9, 2016

(65) Prior Publication Data
US 2017/0367357 A1    Dec. 28, 2017

(30) Foreign Application Priority Data
Dec. 5, 2014 (JP) .................................. 2014-247308

(51) Int. Cl.
A23C 7/04 (2006.01)
A23C 9/12 (2006.01)
(Continued)

(52) U.S. Cl.
CPC .................. *A23C 7/04* (2013.01); *A23C 9/12* (2013.01); *A23C 9/1206* (2013.01); *C12N 1/02* (2013.01);
(Continued)

(58) Field of Classification Search
CPC ........... A23C 7/04; A23C 9/12; A23C 9/1203; A23C 9/1206; C12N 1/02; C12Y 302/01108
(Continued)

(56) References Cited

U.S. PATENT DOCUMENTS 4,237,230 A * 12/1980 Iida et al.
2004/0121041 A1   6/2004 Van Beckhoven et al.
(Continued)

FOREIGN PATENT DOCUMENTS

CN    103451167 A    12/2013
EP    1954808 A2    8/2008
(Continued)

OTHER PUBLICATIONS

R. Bemvenuti Heidtmann et al: "Caracterização cinética e termodinâmica de ß-galactosidase de Kluyveromyces marxianus CCT 7082 fracionada com sulfato de amônio", Brazilian Journal of Food Technology, pp. 41-49, Mar. 2012 (9 pages).
(Continued)

*Primary Examiner* — Helen F Heggestad
(74) *Attorney, Agent, or Firm* — Osha Liang LLP

(57) ABSTRACT

[Problem] To provide a lactase solution having excellent thermal stability.

[Solution] A lactase solution in which the ratio of a lactase fraction having a molecular weight of about 120 kDa measured by SDS polyacrylamide gel electrophoresis is 20% or more.

17 Claims, 5 Drawing Sheets

① Example 1-1
② Example 1-2
③ Comparative Example 1-1
④ Comparative Example 1-2
⑤ Comparative Example 2
⑥ Comparative Example 3

(51) Int. Cl.
*C12N 1/02* (2006.01)
*C12N 9/38* (2006.01)
*G01N 27/447* (2006.01)

(52) U.S. Cl.
CPC .... *C12N 9/2468* (2013.01); *C12Y 302/01108* (2013.01); *G01N 27/44747* (2013.01)

(58) Field of Classification Search
USPC .............................. 426/42, 43, 52, 491, 580
See application file for complete search history.

(56) References Cited

U.S. PATENT DOCUMENTS

| 2010/0143535 | A1* | 6/2010 | Motoshima et al. |
| 2011/0117243 | A1 | 5/2011 | Ur-Rehman et al. |
| 2011/0212221 | A1* | 9/2011 | Beckoven et al. |
| 2015/0359239 | A1 | 12/2015 | Van Beckhoven et al. |

FOREIGN PATENT DOCUMENTS

| EP | 2010654 | A2 | 1/2009 |
| EP | 2439266 | A2 | 4/2012 |
| EP | 2439267 | A2 | 4/2012 |
| EP | 2977453 | A1 | 1/2016 |
| JP | S53-24094 | A | 3/1978 |
| JP | S60-18394 | B2 | 5/1985 |
| JP | 2004-534527 | A | 11/2004 |
| JP | 2009-517061 | A | 4/2009 |
| WO | 2007/060247 | A2 | 5/2007 |
| WO | 2007/122210 | A2 | 11/2007 |
| WO | 2010092057 | A1 | 8/2010 |
| WO | 2011150754 | A1 | 12/2011 |
| WO | 2013/168438 | A1 | 11/2013 |

OTHER PUBLICATIONS

R. C. Dickson et al: "Purification and Properties of an Inducible ß-Galactosidase Isolated from the Yeast Kluyveromyces lactis", Journal of Bacteriology, vol. 137, No. 1, pp. 51-61, Jan. 1979 (11 pages).
A. Nath et al: "Purification and Characterization of ß-Galactosidase Synthesized from Bacillus safensis (JUCHE 1)", Industrial & Engineering Chemistry Research., vol. 52, pp. 11663-11672, Jun. 19, 2013 (10 pages).
M. Becerra et al: "Dealing with different methods for Kluyveromyces lactis ß-galactosidase purification", Biological Procedures Online, vol. 1, No. 1, pp. 48-58, May 14, 1998 (11 pages).
S. Bansal et al: "Production of ß-galactosidase by Kluyveromyces marxianus MTCC 1388 using whey and effect of four different methods of enzyme extraction on ß-galactosidase activity", Indian Journal of Microbiology, vol. 48, pp. 337-341, Jun. 2008 (5 pages).
Extended European Search Report issued in European Patent Application No. 15864455.9; dated Apr. 16, 2018 (11 pages).
L. Hussein et al. "Reduction of Lactose in Milk by Purified Lactase Produced by Kluyveromyces lactis", Journal of Food Protection, vol. 52, No. 1, Jan. 1988, pp. 30-34 (5 pages).
Office Action issued in New Zealand Application No. 732456, dated May 16, 2018 (4 pages).
Office Action issued in N.Z. Application No. 732456; dated Feb. 8, 2018 (4 pages).
Li, B. et al. Preparation of lactose-free pasteurized milk with a recombinant thermostable B-glucosidase from Pyrococcus furiosus. BMC biotech 13:73 p. 1-10 (10 pages).
Borglum, G. et al., "Properties of a fungal Lactase", Journal of Food Science, vol. 37, (1972) pp. 619-623, (5 pages).
Office Action issued in N.Z. Application No. 732456; dated Nov. 28, 2017 (4 pages).
International Search Report issued in corresponding application No. PCT/JP2015/082784 dated Feb. 2, 2016 (6 pages).
Written Opinion of the International Searching Authority issued in corresponding application No. PCT/JP2015/082784 dated Feb. 2, 2016 (5 pages).
O'Connell S. et al., "A novel acid-stable, acid-active ß-galactosidase potentially suited to the alleviation of lactose Intolerance"; Applied Microbiology Biotechnology, vol. 86, No. 2, pp. 517-524, Figure 1; 2010 (8 pages).
Katrolia P. et al., "Molecular cloning and high-level expression of a ß-galactosidase gene from Paecilomyces aerugineus in Pichia pastoris"; Journal of Molecular Catalysis B: Enzymatic, vol. 69, pp. 112-119, Figure 2; Jan. 2011 (8 pages).
Poch et al., "Sequence of the Kluyveromyces lactic ß-galactosidase: comparison with prokaryotic enzymes and secondary structure analysis"; Gene, 118, pp. 55-63; 1992 (9 pages).
Y. Fujimura et al., "Purification and molecular characterization of ß-galactosidase from yeast Kluyveromyces lactis," J. Biol. Macromol., 3 (3) 97-103, 2003 (7 pages).
Office Action issued in counterpart Columbian Patent Application No. NC2017/0006191; dated Sep. 21, 2018 (22 pages).
International Preliminary Report on Patentability issued in International Application No. PCT/JP2015/082784 dated Jun. 15, 2017 (9 pages).

* cited by examiner

[Fig. 1]
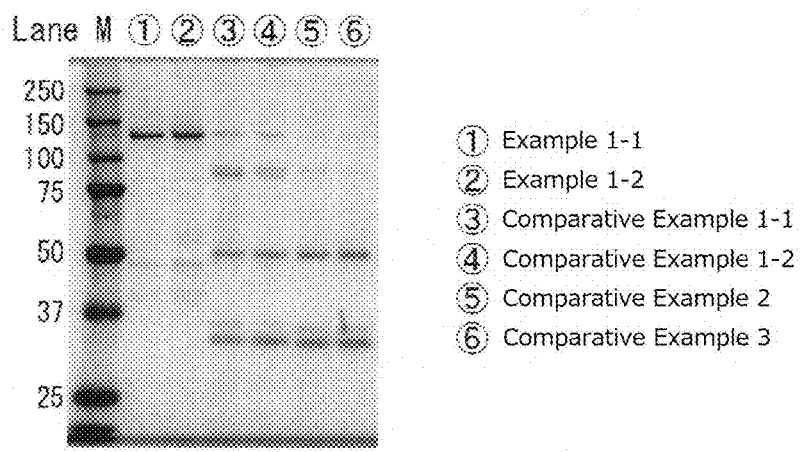
[Fig. 2]
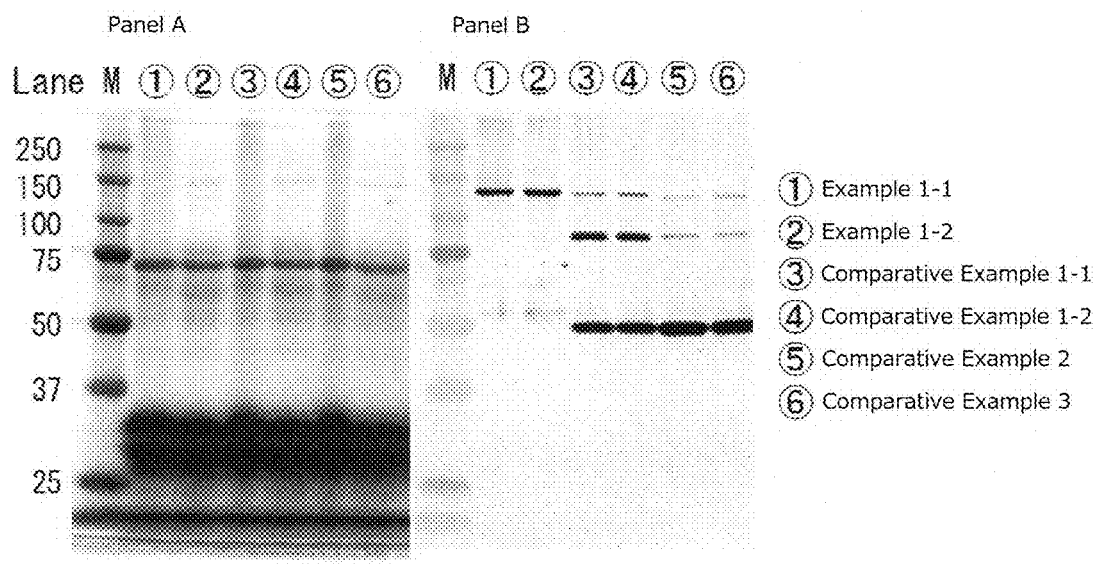

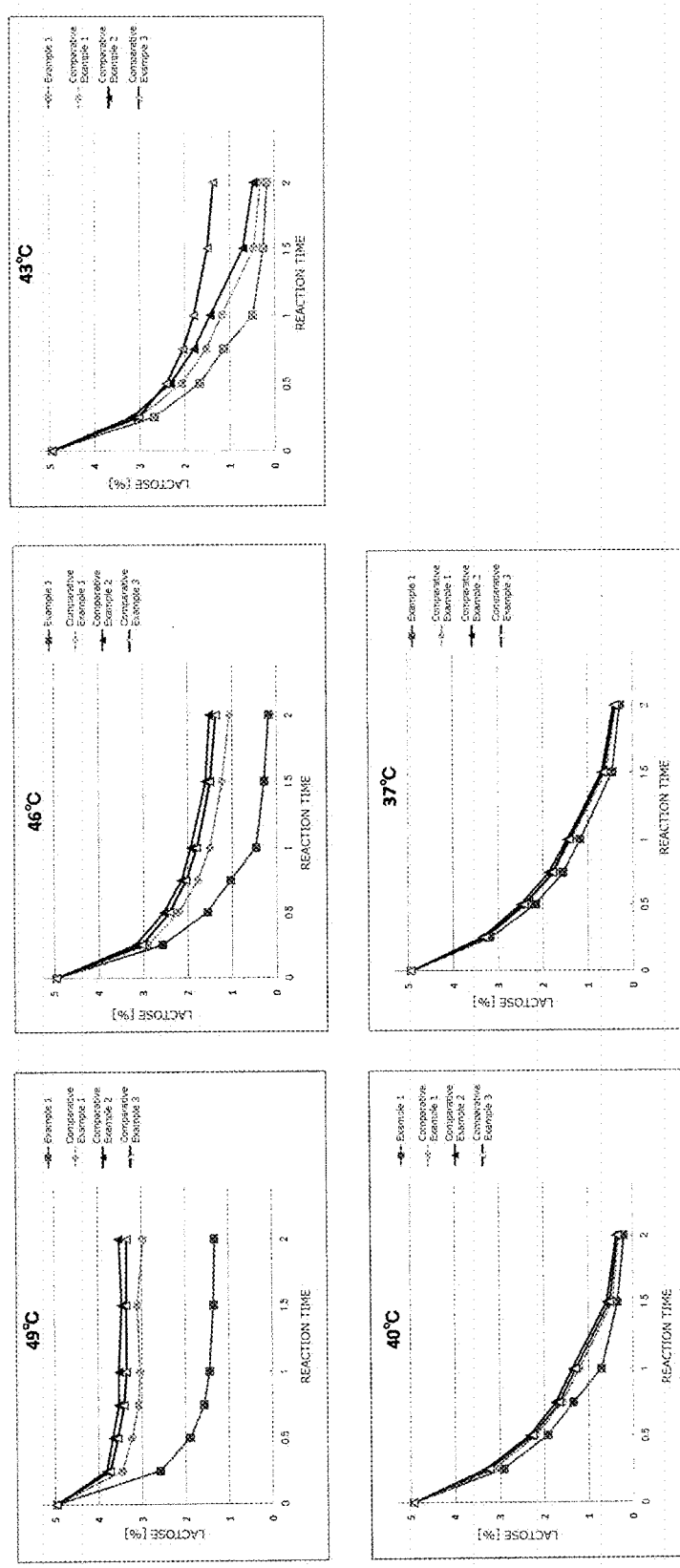
[Fig. 3A]

[Fig. 3B]
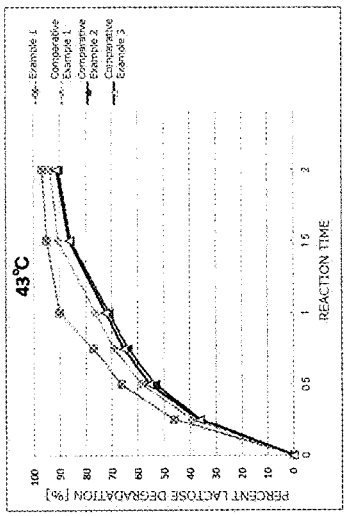
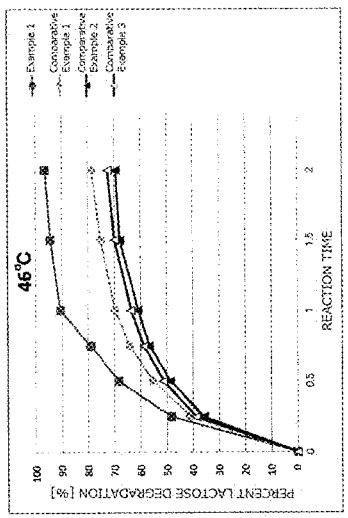
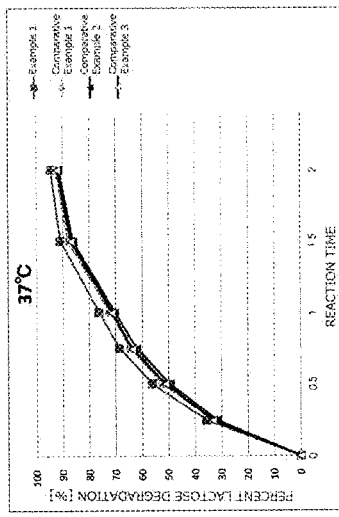
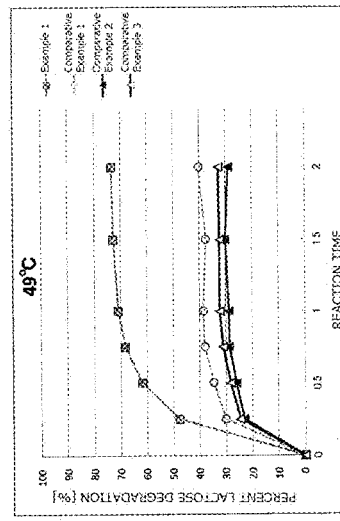
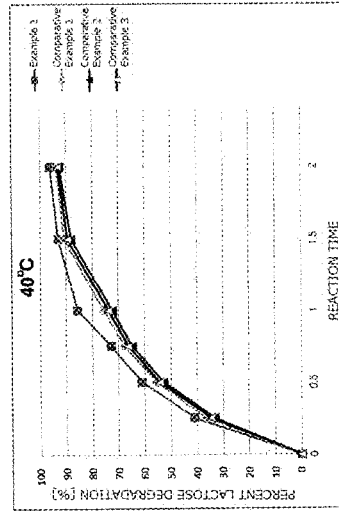

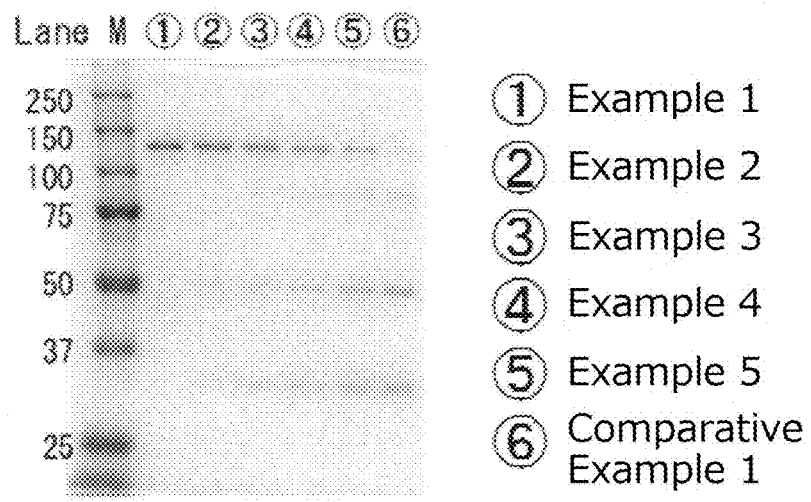
[Fig. 4]

[Fig. 5]
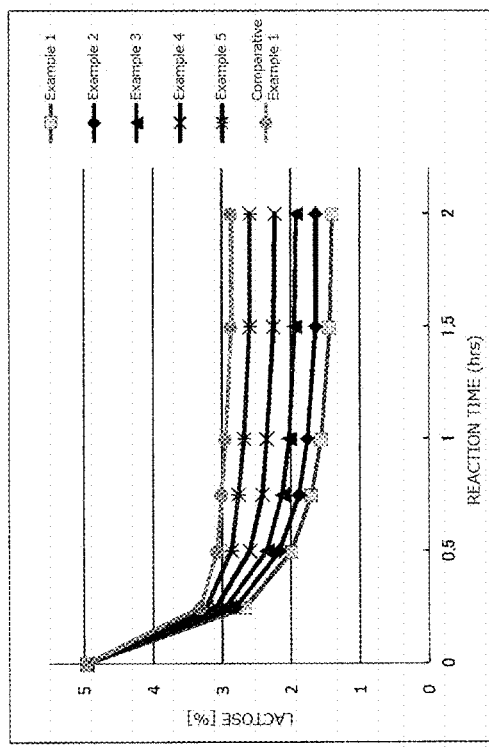
Panel A
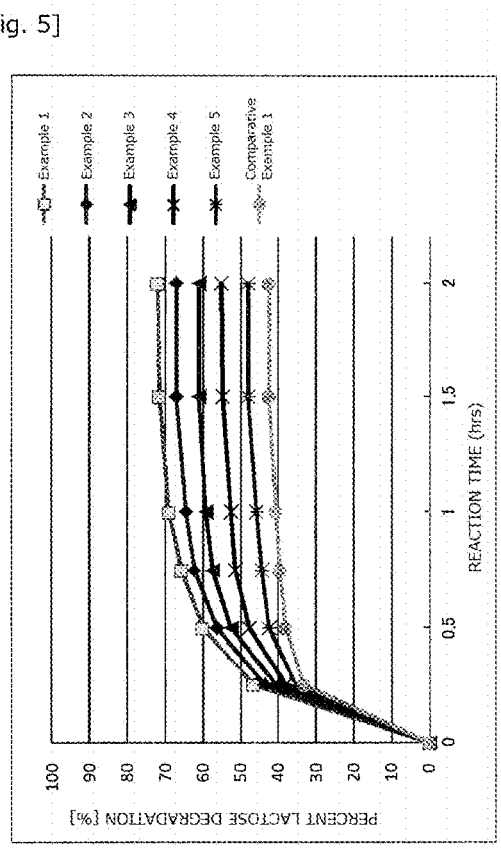
Panel B

LACTASE SOLUTION AND DAIRY PRODUCT USING SAME

TECHNICAL FIELD

The present invention relates to a lactase solution, and milk and dairy products using the same.

BACKGROUND ART

Lactose intolerance is a condition exhibiting various symptoms such as abdominal pain and diarrhea caused by lactose present in a food product such as a dairy product due to congenital insufficiency of decomposing lactose. Lactose is a disaccharide composed of galactose and glucose. In order to address lactose intolerance, decomposing in advance the lactose contained in milk or the like to galactose and glucose using the lactase enzyme is carried out in the food manufacturing industry.

Lactase solutions that are used for decomposing lactose contained in milk or the like is conventionally produced by culturing a lactase-producing microorganism, extracting the lactase from the inside of the cells, removing culture-derived contaminants, and purifying the lactase, followed by addition of a stabilizer and then filter sterilization.

Patent Literature 1 (JP S60-18394 B) discloses an invention which is directed to a method for producing lactase from a culture of a certain strain of *Kluyveromyces lactis*. According to this method, after autolysis of the yeast cells, the resulting crude enzyme solution is passed through a DEAE-cellulose column, resulting in a separation into two active fractions (lactases A and B) by elution with a concentration gradient of NaCl. Patent Literature 1 discloses that these two active fractions are little different in enzymatic properties including thermostability, except that they have a slight difference in pH stability, and thus an enzyme preparation can include a mixture of these active fractions.

From results of the genetic analysis of lactase derived from *Kluyveromyces lactis*, the lactase is a polypeptide consisting of 1,025 amino acids and its molecular weight is presumed to be 117,618 (Non-Patent Literature 1).

It is further described in Patent Literature 1 that the lactase described therein has an optimum temperature of 40 to 50° C. and is inactivated 45% after 10 minute at 50° C. and 100% after 10 minutes at 55° C. at pH 7.0. However, it is not described therein that this enzyme was actually used to decompose the lactose contained in milk. Therefore, Patent Literature 1 describes nothing about the problem of the decrease in enzyme activity when lactase is added to a raw material milk, in particular inactivation of the enzyme when it is subjected to heat load at or above 40° C. in the milk.

CITATION LIST

Patent Literature

Patent Literature 1: JP S60-18394 B
Patent Literature 2: JP 2004-534527 A
Patent Literature 3: JP 2009-517061 A

Non Patent Literature

Non-Patent Literature 1: Poch et al., Gene 1992 Sep. 1; 118(1):55-63

SUMMARY OF INVENTION

Technical Problem

The present invention is aimed at providing a lactase solution that is superior in thermal stability.

Solution to Problem

The present inventors have found that a lactase has high thermal stability by increasing, among lactase species, the ratio of a lactase fraction forming a band at about 120 kDa on SDS polyacrylamide gel electrophoresis (SDS-PAGE), leading to the completion of the present invention.

Therefore, according to the present invention, there are provided:

[1] A lactase solution comprising a lactase fraction having a molecular weight of about 120 kDa measured by SDS polyacrylamide gel electrophoresis in a ratio of 20% or more;

[2] The lactase solution according to [1], wherein the sum of the ratio of the 120-kDa lactase fraction and a ratio of a lactase fraction having a molecular weight of about 80 kDa measured by SDS polyacrylamide gel electrophoresis is 30% or more;

[3] The lactase solution according to [1], wherein a ratio of a lactase fraction having a molecular weight of about 50 kDa measured by SDS polyacrylamide gel electrophoresis is 70% or less;

[4] The lactase solution according to any one of [1] to [3], wherein a value obtained by dividing the sum of the ratio of the about 120-kDa lactase fraction and the ratio of the about 80-kDa lactase fraction by the ratio of the lactase fraction having the molecular weight of about 50 kDa based on SDS polyacrylamide gel electrophoresis is 0.5 or more;

[5] The lactase solution according to any one of [1] to [4], for use in producing dairy products;

[6] A dairy product containing the lactase solution according to any one of [1] to [5];

[7] A method for treating a raw material milk, including adding to a raw material milk the lactase solution according to any one of [1] to [5], and decomposing lactose contained in the raw material milk at 1 to 60° C.;

[8] A method for producing a lactase solution, including
a culture step in which a microorganism is cultured,
a collection step in which the lactase is collected from the culture product obtained in the culture step, and
a purification step in which the lactase collected in the collection step is purified, wherein
the purification step includes one or more cycles of:
a step in which a salting-out treatment and a desalting treatment are carried out;

[9] The method for producing the lactase solution according to [8], wherein the salting-out treatment includes
a saturation step in which to the collected lactase is added a salting-out agent to a degree of saturation of 10 to 90%, and
a keeping step in which after the saturation step, the lactase is allowed to stand at a temperature of 4 to 40° C. for a period of 1 to 80 hours; and

[10] The method for producing the lactase solution according to [8] or [9], wherein the salting-out treatment is carried out at pH 4 to 9.

Advantageous Effects of Invention

According to the present invention, there is provided a lactase solution in which the activity to decompose lactose is hardly reduced even when it is added to a raw material milk and subjected to heat load at or above 40° C.

BRIEF DESCRIPTION OF DRAWINGS

FIG. 1 shows the results of SDS-PAGE of various lactase solutions. Lane 1: Example 1-1, lane 2: Example 1-2, lane 3: Comparative Example 1-1, lane 4: Comparative Example 1-2, lane 5: Comparative Example 2, lane 6: Comparative Example 3, and lane M: molecular weight standards. Lanes 1 and 2, and lanes 3 and 4 show the results from different lots of lactase solutions.

FIG. 2 shows the results of SDS-PAGE (panel A) and Western blotting (panel B) of lactose decomposition reactions in which lactase solutions were added to raw material milk at 43° C. for 2 hours. In each of the panels, lane 1: Example 1-1, lane 2: Example 1-2, lane 3: Comparative Example 1-1, lane 4: Comparative Example 1-2, lane 5: Comparative Example 2, lane 6: Comparative Example 3, and lane M: molecular weight standards.

FIG. 3A represents graphs showing changes over time in the amount of lactose during the reaction in which a lactase solution was added to raw material milk at 37, 40, 43, 46, and 49° C. to decompose lactose contained therein. In the graphs, the results are plotted with □ for Example 1, ○ for Comparative Example 1, ▲ for Comparative Example 2, and Δ for Comparative Example 3.

FIG. 3B represents graphs showing changes over time in the percent lactose decomposition during the reaction in which a lactase solution was added to raw material milk at 37, 40, 43, 46, and 49° C. to decompose lactose contained therein. In the graphs, the results are plotted with □ for Example 1, ○ for Comparative Example 1, ▲ for Comparative Example 2, and Δ for Comparative Example 3.

FIG. 4 shows the results of SDS-PAGE of lactase solutions having different ratios of the 120-kDa lactase fraction. Lane 1: Example 1-1, lane 2: Example 2, lane 3: Example 3, lane 4: Example 4, lane 5: Example 5, lane 6: Comparative Example 1, and lane M: molecular weight standards.

FIG. 5 represents graphs showing changes over time in the amount (panel A) and the percent decomposition (panel B) of lactose during the reaction in which a lactase solution having a different ratio of the 120-kDa lactase fraction was added to raw material milks at 49° C. to decompose lactose contained therein. In the graphs, the results are plotted with □ for Example 1, ♦ for Example 2, ▲ for Example 3, x for Example 4, * for Example 5, and ○ for Comparative Example 1.

DESCRIPTION OF EMBODIMENTS

The lactase that is used in the present invention is one of lactases derived from yeasts (of the genus *Kluyveromyces*). Most of these lactases are so-called neutral lactases having an optimum pH which is of from pH=6 to pH=8. Lactase producing yeasts of the genus *Kluyveromyces* are, for example, *Kluyveromyces lactis*, *Kluyveromyces fragillis*, and *Kluyveromyces marxianus*.

A lactase solution of the present invention desirably has a lactase activity of 10 to 100,000 NLU/g. "NLU" stands for Neutral Lactase Unit. The method for measurement of lactase activity is as follows: The enzyme activity of a lactase solution is determined by hydrolysis of a substrate o-nitrophenyl-β-galactopyranoside (ONPG) into o-nitrophenol and galactose. The reaction is stopped by addition of sodium carbonate. Since the resulting o-nitrophenol is yellow in color in an alkaline medium, changes in absorbance are used to determine the enzyme activity (expressed as NLU/g). This procedure is published in Food Chemicals Codex (FCC), 4th ed., Jul. 1, 1996, pp. 801-802, Lactase (neutral) (β-galactosidase) activity.

A lactase solution of the present invention can be one including a lactase that has been collected from a microorganism by the following method and purified.

The method for producing a lactase solution of the present invention undergoes four steps, that is, (1) a step in which a microorganism is cultured, (2) a step in which the lactase is collected from the microorganism, (3) a step in which the lactase is purified, and (4) a step in which the lactase activity of the lactase solution is adjusted.

The following gives a detailed explanation of these four steps.

Regarding (1) a step in which a microorganism is cultured, this step can be performed employing a known medium and using a known microbial strain. Culture conditions are also known, and can be selected as needed and as appropriate.

Regarding (2) a step in which the lactase is collected from the microorganism, it is necessary that this step includes a step of extracting the lactase from the microorganism when it is an intracellular enzyme. The extraction step is not limited in particular, as long as a method is used, which is capable of transferring the lactase to the outside of the cell, and known extraction methods can be used. On the other hand, if the lactase is an enzyme that is secreted outside the cell of a microorganism modified by gene transfer, mutagenesis, or the like, then its cultured medium will contain the lactase, and thus the extraction step is not required.

Regarding (3) a step in which the lactase is purified, this step is important in order to obtain a lactase solution of the present invention. Patent Literatures 1, 2, and 3 are common in that each of these literatures uses chromatographic procedures to purify a lactase solution. These chromatographic procedures advance the purification of the lactase, making it possible that the lactase solution has an increased lactase activity. However, as described below, when chromatographic procedures, such as partition or molecular sieve chromatography, adsorption chromatography, or ion-exchange chromatography, were used to purify lactase, it turned out that the original lactase of 120 kDa became decomposed into two lactase species of 80 kDa and 50 kDa. Both the lactase species having such molecular weights exhibit lactase activity; however, decomposition of the original lactase leads especially to an increase in the ratio of a 50-kDa lactase fraction, reducing the thermal stability of the lactase and as a result, giving rise to a problem that it becomes difficult that the decomposition of lactose proceeds at relatively high temperatures.

The lactase of the present invention can be obtained by using salting out and desalting treatments in the purification step. For example, the lactase of the present invention is obtained by precipitating the lactase by salting out, followed by collecting and re-dissolving the precipitate, and then desalting the lactase to remove the salts contained therein. Salting out of the lactase, and collecting and re-dissolution of and desalting of the precipitate can be carried out in a continuous manner. It is also possible to use in combination other purification procedures, including chromatography and active carbon treatments, as long as the lactase of the present invention is obtained.

The reason why the 120-kDa lactase species does not become decomposed by salting out is assumed to be that salting out allows the lactase to precipitate as macromolecules and to become insoluble, and thus the lactase has a decreased reactivity to decomposition.

Salting-out agents for salting out lactase include ammonium sulfate, sodium sulfate, potassium phosphate, magnesium sulfate, sodium citrate, sodium chloride, and potassium chloride. These agents can be used alone in combination of two or more.

When ammonium sulfate as a salting-out agent is added to a lactase containing solution, ammonium sulfate is added thereto, preferably to a degree of saturation of 10 to 90%, further preferably 30 to 70%. In cases where a different salting-out agent is used, it can be added in an amount which corresponds to that of ammonium sulfate added.

The lactase can be precipitated out of a lactase containing solution by addition of a salting-out agent such as ammonium sulfate. It is preferable that from the addition of a salting-out agent to when the lactase has been precipitated, the lactase containing solution is allowed to stand at a temperature of 1 to 40° C. for a period of 1 to 80 hours. For pH conditions during this period, a pH of 4 to 9 is preferable. Further preferably, the lactase containing solution is allowed to stand at a temperature of 4 to 25° C. (room temperature) for a period of 1 to 48 hours at a pH of 5 to 8. The lower limit of temperature conditions can be set to a temperature at which the lactase containing solution does not become solidified. The liquid from which the lactase has been precipitated and the lactase containing precipitate are solid-liquid separated by filtration, and then the lactase in the form of solid is dissolved in water, buffer, or the like, and desalted by dialysis or by ultrafiltration concentration.

Regarding (4) a step in which the lactase activity of the lactase solution is adjusted, there is no limitation, as long as the lactase activity of the lactase solution can be adjusted. For example, this step includes addition of water, addition of aqueous solutions containing salts, addition of stabilizer, and the like.

A lactase solution of the present invention can also be obtained by mixing a commercially available lactase solution and a lactase solution obtained by the above-described method, as long as the ratios of lactase fractions with specified molecular weights measured by SDS polyacrylamide gel electrophoresis meet to be within particular ratios.

The molecular weight of lactase species in a lactase solution can be roughly determined by SDS-PAGE using a 10% polyacrylamide gel. For example, a sample of a lactase solution is diluted in purified water, if necessary, and mixed 1:1 with an SDS-PAGE sample buffer, and the mixture is heated at 95 degrees for 5 minutes to prepare an electrophoresis sample. A 10% acrylamide gel is loaded with standards and the prepared electrophoresis sample, and subjected to electrophoresis. The standards use, for example, BIO-RAD #161-0313 (pre-stained) standards. The gel after electrophoresis is subjected to protein staining with a CBB staining solution (APRO SP-4010).

After a lactase solution of the present invention is subjected to SDS-PAGE and CBB staining, the gel is dried using the TEFCO polyacrylamide drying kit (a trade name of Clear Dry Solution). The dried gel is scanned as a gray-scale image with an EPSON scanner GT-X820, on which the densities of stained protein bands (corresponding to protein amounts) are determined using the Image J software (NIH, Bethesda, Md.).

A lactase solution of the present invention has a high ratio of a lactase fraction having a molecular weight of about 120 kDa when determined by the above-described method. In the present invention, a "lactase fraction having a molecular weight of about 120 kDa measured by SDS polyacrylamide gel electrophoresis" refers to a fraction of a lactase species forming a band located at a position corresponding to about 120 kDa (or in a range between about 100 kDa and about 150 kDa), relative to the mobilities of molecular weight standards, after electrophoresis is performed using the above-described method.

For a lactase solution of the present invention, the ratio of an about 120-kDa lactase fraction determined by the Image J software (NIH, Bethesda, Md.) after SDS-PAGE and CBB staining is 20% or more, preferably 50% or more, further preferably 80% or more, and most preferably 90% or more. Its upper limit is not particularly limited, but, for example, 100%. The ratio of such a lactase fraction is calculated by the method described below.

After SDS-PAGE and CBB staining, the Image J software (NIH, Bethesda, Md.) is used to quantify the densities of stained protein bands to calculate the ratio of a stained protein bands corresponding to about 120 kDa on the basis of the total main bands as 100%, including stained protein bands corresponding to about 120 kDa (100 to 150 kDa), about 80 kDa (80 to 100 kDa), about 50 kDa (49 to 54 kDa), and about 30 kDa (28 to 32 kDa). The values recited in claims of the present application are values calculated when the total of these four stained protein bands is set to be 100% unless specifically recited.

For a lactase solution of the present invention, the sum of the ratio of an about 80-kDa lactase fraction calculated using the above-described method and the ratio of the above-described 120-kDa lactase fraction, preferably is 30% or more, more preferably 60% or more, further preferably 90% or more. Its upper limit is not particularly limited, but for example, 100%.

The decomposition of a lactase species of about 120 kDa (which may be referred to hereinafter as lactase I) generates a lactase species of about 80 kDa (which may be referred to hereinafter as lactase II), and the decomposition of lactase I or II generates a lactase species of about 50 kDa (which may be referred to hereinafter as lactase III).

Lactases I and II in a lactase solution each have lactase activity and heat resistance. Lactase III has lactase activity, but is poor in heat resistance. Any of these lactase fractions has comparable lactase activity.

Since lactase II is a decomposition product of lactase I, it is preferable that the ratio of lactase I in a lactase solution is larger than that of lactase II from a viewpoint of heat resistance.

The ratio of lactase III in a lactase solution preferably is 70% or less, more preferably 40% or less, further preferably 10% or less. Its lower limit is not particularly limited, but for example 0%.

The value obtained by dividing the sum of the ratios of lactases I and II by the ratios of lactase III preferably is 0.5 or more, more preferably 1.0 or more, further preferably 5.0 or more. When the value is less than 0.5, there is a tendency that the lactase solution exhibits insufficient heat resistance. Its upper limit is not limited because it is most preferable that the lactase solution contains no lactase III, that is, zero amounts of lactase III.

A raw material milk is a subject to which the lactase solution is to be added. In the present invention, known raw material milks can be employed. Raw material milks also include ones before and after pasteurization. Any raw material milk can be used, as long as it is obtained using a milk. Ingredients composing raw material milks are water, raw milk, pasteurized milk, defatted milk, dry whole milk, non-fat dry milk, buttermilk, butter, cream, whey protein concentrates (WPCs), whey protein isolates (WPIs), α (alpha)-La, β (beta)-Lg, and the like.

The lactose contained in a raw material milk can be decomposed by adding thereto a lactase solution of the present invention. The decomposition temperature is 1 to 60° C. and the decomposition time is 10 minutes to 24 hours.

Examples of specific usages of a lactase solution include, for example, use in the production of a fermented milk. Methods for producing a lactose-decomposed fermented milk include: for example, 1. a method in which a lactase solution is added to a milk before pasteurization, thereby to decompose lactose, followed by heat pasteurization of the milk and concomitant inactivation of the lactase, followed by fermentation of the treated milk (JP Hei 5-501197 A); 2. a method in which a lactase solution is added to a pasteurized milk, thereby to decompose lactose, followed by heat treatment to inactivate the lactase, followed by fermentation of the treated milk; 3. a method in which the lactose in a milk is decomposed by an immobilized lactase, followed by fermentation of the treated milk (JP S46-105593 A and S59-162833 A); and 4. a method in which a raw material that has been subjected beforehand to decomposition or removal of lactose is used as a pasteurized milk, followed by fermentation.

A lactase solution according to the present invention is particularly suitable for use in the production of dairy products. Here, dairy products refer to ice cream, milks such as long life milk, yogurt, fresh cream, sour cream, cheese, and others. Particularly, a lactase solution according to the present invention can preferably be used when exposed to heat load at or above 40° C. Such use includes, for example, use in the production of yogurts.

EXAMPLES

1. Production of Lactase Solutions

Example 1

A liquid medium containing 7% corn steep liquor and 2% lactose was pressure-sterilized (and had a pH of 5.5 after sterilization), and was inoculated with *Kluyveromyces lactis* No. 013-2 (strain ATCC 8585), which was cultured at 30° C. for 24 hours under aeration at 12000 L/min. After completion of the culturing, the culture broth was left to stand for 4 hours with cooling. Then, the supernatant was removed from the top of the fermentation tank to obtain 1500 kg of cells, which had aggregated and settled down at the bottom of the tank. Then, 1500 g of thus obtained cells were washed with tap water. After that, 80 ml toluene was added to and mixed with the cells, followed by addition of 1500 ml of 0.05 M phosphate buffer (pH 7.0). The mixture was stirred to make a homogeneous suspension, which then was left to stand, under hermetic sealing, at 30° C. for 15 hours for cell autolysis.

The resulting autolysis product was centrifuged to obtain 2500 ml supernatant, to which an equal volume of cold acetone was added, and the mixture was left to stand overnight. The resulting precipitates were collected by centrifugation, and then dissolved in 600 ml tap water to prepare an enzyme solution before concentration.

To the enzyme solution (600 ml) before concentration, with cooling to 4° C., was added ammonium sulfate powder in portions over 60 minutes to make an aqueous solution that was 50% saturated therewith. The aqueous solution was left to stand (left standing) at 4° C. for 80 hours to allow the lactase to settle down, followed by solid-liquid separation by filtration to collect the lactase in the form of solid. The lactase was re-dissolved in 600 ml tap water, followed by ultrafiltration concentration. To the resulting desalted lactase solution was added tap water, followed by addition of glycerin to a final concentration of 50% to prepare a lactase solution (5,000 NLU/g) of Example 1.

Example 2

The lactase solution of Example 1 and a lactase solution of Comparative Example 1 described below were mixed at a ratio by weight of 80:20 to prepare a lactase solution (5,000 NLU/g) of Example 2.

Example 3

The lactase solution of Example 1 and a lactase solution of Comparative Example 1 described below were mixed at a ratio by weight of 60:40 to prepare a lactase solution (5,000 NLU/g) of Example 3.

Example 4

The lactase solution of Example 1 and a lactase solution of Comparative Example 1 described below were mixed at a ratio by weight of 40:60 to prepare a lactase solution (5,000 NLU/g) of Example 4.

Example 5

The lactase solution of Example 1 and a lactase solution of Comparative Example 1 described below were mixed at a ratio by weight of 20:80 to prepare a lactase solution (5,000 NLU/g) of Example 5.

Comparative Example 1

A commercially available lactase preparation, which is available as a trade name of "GODO-YNL 2SS" (manufactured by GODO SHUSEI CO., LTD.; 5000 NLU/g), was used to prepare a lactase solution of Comparative Example 1.

Comparative Example 2

A commercially available lactase preparation, which is available as a trade name of "MAXILACT LG 5000" (manufactured by DSM; 5000 NLU/g), was used to prepare a lactase solution of Comparative Example 2.

Comparative Example 3

A commercially available lactase preparation, which is available as a trade name of "MAXILACT LGX 5000" (manufactured by DSM; 5000 NLU/g), was used to prepare a lactase solution of Comparative Example 3.

2. Electrophoresis of Lactase Solutions

Each of these lactase solutions was diluted in milli-Q water to have a lactase activity of 10 NLU/g, and mixed 1:1 with an SDS-PAGE sample buffer (0.125 M Tris-HCl, pH 6.8, 0.0125% bromothymol blue, 20% glycerin, 2.5% SDS, 2.5% 2-mercaptoethanol), and the mixture was heated at 95° C. for 5 minutes to prepare an electrophoresis sample. A 10% acrylamide gel (4% stacking gel, a thickness of 1 mm, an electrophoresis distance of 50 mm) was loaded with molecular weight standards and the prepared samples and subjected to electrophoresis in a Marisol Industry electrophoresis apparatus, which was run at a constant current of 10 mA in the stacking gel and 20 mA in the separating gel until the running front reached almost the lower end of the gel. The molecular weight standards (lane M) used BIO-RAD #161-0313 (pre-stained) standards. The gel after electrophoresis was subjected to protein staining for 1 hour with a CBB staining solution (APRO SP-4010).

The results are shown in FIG. 1. For the lactase solution of Example 1 (lanes 1 and 2), only a main band with a molecular weight of about 120 kDa was observed. In contrast, for the lactase solution of Comparative Example 1 (lanes 3 and 4), a band with a molecular weight of about 120 kDa almost disappeared, while three bands with molecular weights of about 80 kDa, about 50 kDa, and about 30 kDa were detected as main bands. For the lactase solutions of both Comparative Examples 2 (lane 5) and 3 (lane 6), in addition to a band with a molecular weight of about 120 kDa, a band with a molecular weight of about 80 kDa was almost not observed, and there were observed main bands at about 50 kDa and about 30 kDa.

Lactase activity was detected for bands with molecular weights of about 120 kDa, about 80 kDa, and about 50 kDa, and not for a band with a molecular weight of about 30 kDa.

3. Quantitative Determination of Each of the Lactase Bands and Results 1

The ratios of the respective lactase bands on the gel after electrophoresis were calculated based on their quantitative determination using the above-described method. The results are shown in Table 1. Table 1 lists calculated values for four lactase main bands on the basis of all the protein bands. Furthermore, Table 2 shows the results of the calculated ratios of the respective lactase bands on the basis of only four lactase main bands in total. In Tables 1 to 4, the reason why the sum of the values for the lactase solutions of the Examples and Comparative Examples is not 100 is that their respective measurements obtained were rounded off to one decimal place.

Although not shown in Tables 1 and 2, when fractions A and B obtained by repeating Example 1 of Patent Literature 1 were analyzed by electrophoresis as with Example 1 and others of the present invention, these fractions had a similar tendency to those observed for Comparative Examples 2 and 3 of the present invention.

TABLE 1

|  | Example 1-1 | Example 1-2 | Comparative Example 1-1 | Comparative Example 1-2 | Comparative Example 2 | Comparative Example 3 |
|---|---|---|---|---|---|---|
| About 120,000 | 78.8 | 76.6 | 13.0 | 8.7 | 3.9 | 3.5 |
| About 80,000 |  |  | 23.9 | 14.1 | 5.3 | 3.5 |
| About 50,000 |  |  | 25.7 | 32.6 | 36.7 | 37.9 |
| About 30,000 |  |  | 37.5 | 43.0 | 53.7 | 55.1 |
| Others | 21.2 | 23.5 |  | 1.6 | 0.4 |  |

TABLE 2

|  | Example 1-1 | Example 1-2 | Comparative Example 1-1 | Comparative Example 1-2 | Comparative Example 2 | Comparative Example 3 |
|---|---|---|---|---|---|---|
| About 120,000 | 100.0 | 100.0 | 13.0 | 8.9 | 3.9 | 3.5 |
| About 80,000 |  |  | 23.9 | 14.3 | 5.3 | 3.5 |
| About 50,000 |  |  | 25.7 | 33.1 | 36.9 | 37.9 |
| About 30,000 |  |  | 37.5 | 43.7 | 53.9 | 55.1 |

4. Electrophoresis and Western Blot Analyses of Milks after Lactose Decomposition Reaction To a milk that had gone through UHT pasteurization (at 130° C. for 2 seconds) (a trade name of "Meiji Oishii Gyunyu", manufactured by Meiji Co., Ltd.) was added the lactase solution of Example 1 (corresponding to lanes 1 and 2), or Comparative Example 1 (corresponding to lanes 3 and 4), 2 (corresponding to lane 5), or 3 (corresponding to lane 6) to a final concentration of 0.05% (w/v), and the mixture was subjected to a lactose decomposition reaction at 43° C. for 2 hours. The solution after the reaction was diluted 20 times (w/v) in purified water, and mixed 1:1 with an SDS-PAGE sample buffer, and the mixture was heated at 95 degrees for 5 minutes to prepare an electrophoresis sample. Two 10% acrylamide gels were loaded with molecular weight standards and the prepared electrophoresis samples, and subjected to electrophoresis in parallel. The molecular weight standards (lane M) used BIO-RAD #161-0313 (pre-stained) standards.

After the electrophoresis, one of the gels was subjected to protein staining with a CBB staining solution as described above, and the other to western blotting. As the western blotting transfer membrane, a nitrocellulose membrane (BIO-RAD #162-0114) was used, and western blotting was carried out in a wet manner. The membrane after the transfer was blocked with a Block Ace solution (4 g Block Ace powder (Snow Brand Milk Products Co., Ltd.) in 100 ml purified water), and then washed with Tween-PBS.

As the primary antibody, an anti-lactase polyclonal antibody was used, which had been prepared in-house as described below. SDS-PAGE was performed using an aliquot of the lactase solution obtained in Example 1, and a portion containing a 120-kDa lactase band was cut out of the gel and crushed, and then mixed with Difco Adjuvant, Complete, Freund, to make an emulsion. The emulsion was subcutaneously injected a total of three times at the base of the tail of Balb-C mice. After an increase in antibody titer in serum was observed, the supernatant obtained by centrifugation of a collected whole blood sample was used as an anti-lactase polyclonal antibody. This antibody was capable of detecting lactase bands with molecular weights of 120, 80, and 50 kDa.

The membrane was subjected to reaction at room temperature for 2 hours in a solution in which the anti-lactase antibody was diluted 1,000 times in a diluted Block Ace solution, which was a 10-times dilution of the Block Ace solution in purified water. The membrane was washed four times with Tween-PBS and then subjected to reaction at room temperature for 2 hours in a solution in which a secondary antibody (gort a-mouse IgG(H+L)-HRP; SouthernBiotech, 1034-05) was diluted 5,000 times in a diluted Block Ace solution. The membrane was washed with Tween-PBS, followed by staining with 3,3'-diaminobenzidine (DAB). For the DAB substrate, a DAB buffer tablet (MERCK, 1.02924.0001) was used as indicated.

The results are shown in FIG. 2. In the CBB staining image (panel A), there were observed almost the same results regardless of the differences of lactase solutions used. In contrast, the results of western blotting (panel B) showed different bands due to the differences of lactase solutions used, as in the case of the lactase solutions before the reaction. That is, for the lactase solution of Example 1, only a main band with a molecular weight of about 120 kDa was observed; for the lactase solution of Comparative Example 1, a band with a molecular weight of about 120 kDa almost disappeared, while two bands with molecular weights of about 80 kDa and about 50 kDa were detected as main bands. For the lactase solution of Comparative Example 2 or 3, in addition to a band with a molecular weight of about 120 kDa, a band with a molecular weight of about 80 kDa was almost not observed, and the main band was observed at about 50 kDa.

Based on the above, there were not found changes in the molecular weights of and in the ratios of molecular weight fractions of the lactase species contained in each of the lactase solutions between before and after subjected to the lactose decomposition reaction.

5. Lactose Decomposition Test 1

To a milk that had gone through UHT pasteurization (at 130° C. for 2 seconds) was added each of the lactase solutions of Example 1 and Comparative Examples 1, 2, and 3 to a final concentration of 0.05% (w/v) (2.5 NLU per 100 mL milk), and the mixture was subjected to a lactose decomposition reaction at 49° C., 46° C., 43° C., 40° C., and 37° C. The contents of lactose in the reaction solutions before and over time during the lactose decomposition reaction were determined by HPLC (using a Transgenomic CARBOSep CHO620 column in the Waters Alliance HPLC system; column temperature: 85° C., solvent: $H_2O$, flow rate: 0.5 mL/min, detector: Waters 2414 RI detector). Percent lactose decomposition was calculated according to the following formula: Percent lactose decomposition (%)=100−[(the content of lactose in the milk after it was subjected to the lactose decomposition reaction using the lactase solution of an Example or Comparative Example)/ (the content of lactose in the milk before it was subjected to the lactose decomposition reaction using the lactase solution of the Example or Comparative Example)×100].

The results are shown in FIG. 3. FIGS. 3A and 3B show the results of changes over time in lactose content and in percent lactose decomposition, respectively. After 2 hours of the lactose decomposition reaction at 37° C., no differences in percent lactose decomposition were observed for the lactase solution of Example 1 or Comparative Example 1, 2, or 3, but there was found a tendency that, as the reaction temperature was increased, the lactase solution of Example 1 gave the highest percent of decomposition of lactose, followed by Comparative Example 1, and the lactase solution of Comparative Example 2 or 3 gave the lowest percent of decomposition of lactose. As has been mentioned, it was shown that also when the reaction temperature was increased, the lactase solution of the present invention exhibited no inactivation of lactase and thus a higher thermal stability. The lactase solution of Example 1 also allows a more efficient decomposition of lactose in a shorter reaction time by increasing the reaction temperature. Also for lactase solutions from different lots according to the present invention, the reproducibility of these findings was verified.

Since the molecular weights of the main lactase fractions in the respective lactase solutions did not change between before and after the lactose decomposition reaction, the decrease in percent lactose decomposition is attributable to the decrease in lactase activity during the reaction. It was also found that the higher the content of the 120-kDa lactase fraction, the higher the percent lactose decomposition in the reactions at or above 40° C.

6. Examinations Using Mixed Lactase Solutions

Examinations were made of the lactase solutions of Examples 2 to 5, which were lactase solutions obtained by mixing the lactase solutions of Example 1 and Comparative Example 1 at the above-described ratios.

6.1 Quantitative Determination of Lactase Bands and Results 2

For the lactase solutions of Examples 2 to 5, electrophoresis was performed by the above-described method, followed by quantitative determination of lactase bands. The results of electrophoresis of the lactase solutions are shown in FIG. 4 and the results of quantitative determination of lactase bands are shown in Table 3. Table 3 lists values for four main lactase bands when all the protein bands were used for calculation. Furthermore, Table 4 shows the results when only the four main lactase bands were used to calculate the ratios of the respective lactase bands. For comparison, Tables 3 and 4 include the results of electrophoresis and quantitative determination that were carried out concurrently for the lactase solutions of Example 1 and Comparative example 1.

TABLE 3

|  | Example 1 | Example 2 | Example 3 | Example 4 | Example 5 | Comparative Example 1 |
|---|---|---|---|---|---|---|
| About 120,000 | 82.8 | 77.8 | 66.5 | 44.3 | 23.8 | 5.5 |
| About 80,000 |  | 1.9 | 2.2 | 6.3 | 7.7 | 12.9 |
| About 50,000 |  | 11.7 | 16.3 | 26.3 | 32.7 | 38.8 |
| About 30,000 |  | 4.9 | 13.8 | 21.9 | 32.5 | 40.8 |
| Others | 17.2 | 3.7 | 1.2 | 1.1 | 3.4 | 2.0 |

TABLE 4

|  | Example 1 | Example 2 | Example 3 | Example 4 | Example 5 | Comparative Example 1 |
|---|---|---|---|---|---|---|
| About 120,000 | 100.0 | 80.8 | 67.3 | 44.8 | 24.6 | 5.7 |
| About 80,000 |  | 2.0 | 2.2 | 6.4 | 7.9 | 13.1 |
| About 50,000 |  | 12.1 | 16.5 | 26.6 | 33.8 | 39.6 |
| About 30,000 |  | 5.1 | 14.0 | 22.2 | 33.6 | 41.7 |

Lactose Decomposition Test 2

The lactase solutions of Examples 1 to 5 and Comparative Example 1 were used for a lactose decomposition reaction at 49° C. by the above-described lactose decomposition test. The results obtained are shown in FIG. 5.

Panels A and B show the results of changes over time in lactose content and in percent lactose decomposition, respectively. It was found that the decomposition of lactose increased with an increasing ratio of the about 120-kDa lactase band.

Therefore, it can be said from the above results that a lactase solution in which the ratio of the main lactase band at about 120 kDa on SDS-PAGE is 20% or more has a higher heat resistance than that giving any of the main lactase bands with molecular weights of about 80 kDa, about 50 kDa, and about 30 kDa on SDS-PAGE.

The invention claimed is:

1. A lactase solution comprising a lactase derived from a yeast of the genus *Kluyveromyces*, the lactase solution comprising a lactase fraction having a molecular weight of about 120 kDa measured by SDS polyacrylamide gel electrophoresis in a ratio of 20% or more,
wherein the sum of the ratio of the about 120 kDa lactase fraction and a ratio of a lactase fraction having a molecular weight of about 80 kDa measured by SDS polyacrylamide gel electrophoresis is 100%.

2. The lactase solution according to claim 1, wherein a ratio of a lactase fraction having a molecular weight of about 50 kDa measured by SDS polyacrylamide gel electrophoresis is 70% or less.

3. A dairy product comprising the lactase solution according to claim 2.

4. A method for treating a raw material milk, comprising adding to a raw material milk the lactase solution according to claim 2, and decomposing lactose contained in the raw material milk at 1 to 49° C.

5. The lactase solution according to claim 1, wherein a value obtained by dividing the sum of the ratio of the about 120-kDa lactase fraction and the ratio of the about 80-kDa lactase fraction by the ratio of the lactase fraction having the molecular weight of about 50 kDa measured by SDS polyacrylamide gel electrophoresis is 0.5 or more.

6. A dairy product comprising the lactase solution according to claim 5.

7. A method for treating a raw material milk, comprising adding to a raw material milk the lactase solution according to claim 5, and decomposing lactose contained in the raw material milk at 1 to 49° C.

8. A dairy product comprising the lactase solution according to claim 1.

9. A method for treating a raw material milk, comprising adding to a raw material milk the lactase solution according to claim 1, and decomposing lactose contained in the raw material milk at 1 to 60° C.

10. The lactase solution according to claim 1, further comprising a stabilizer.

11. The lactase solution according to claim 10, wherein the stabilizer is glycerin.

12. A method for producing the lactase solution claim 1, comprising
culturing a microorganism producing a lactase as an intracellular enzyme,
collecting the lactase from the culture product obtained in the culturing, wherein the collecting comprises extracting the lactase from the microorganism, and
purifying the collected lactase, wherein the purifying includes performing one or more cycles of a step-comprising a salting-out treatment and a desalting treatment.

13. The method for producing the lactase solution according to claim 12, wherein the salting-out treatment comprises:
adding, to the collected lactase, a salting-out agent to a degree of saturation of 10 to 90%; and
allowing, after the adding, the lactase to stand at a temperature of 4 to 40° C. for a period of 1 to 80 hours.

14. The method for producing the lactase solution according to claim 13, wherein the salting-out treatment is carried out at pH 4 to 9.

15. The method for producing the lactase solution according to claim 12, wherein the salting-out treatment is carried out at pH 4 to 9.

16. The method according to claim 12, wherein the lactase is a lactase derived from a yeast of the genus *Kluyveromyces*.

17. The method according to claim 12, wherein the lactase has an optimum pH ranging from 6 to 8.

* * * * *